(12) United States Patent
Schumacher et al.

(10) Patent No.: US 6,506,767 B1
(45) Date of Patent: Jan. 14, 2003

(54) 8-CHLORO-6,11-DIHYDRO-11-(4-PIPERIDYLIDINE)-5H-BENZO[5,6] CYCLOHEPTA[1-2-B] PYRIDINE

(75) Inventors: Doris P. Schumacher, Bedminster, NJ (US); Junning Lee, Gillette, NJ (US); Lawrence R. Rogers, Short Hills, NJ (US); Charles G. Eckhart, Scotch Plains, NJ (US); Naneshwar S. Sawant, Edison, NJ (US); Michael B. Mitchell, Basking Ridge, NJ (US)

(73) Assignee: Schering Corporation, Kenilworth, NJ (US)

( * ) Notice: Subject to any disclaimer, the term of this patent is extended or adjusted under 35 U.S.C. 154(b) by 375 days.

(21) Appl. No.: 09/108,689

(22) Filed: Jul. 1, 1998

Related U.S. Application Data (60) Provisional application No. 60/051,547, filed on Jul. 2, 1997.

(51) Int. Cl.$^7$ .................... C07D 401/08; A61K 31/445
(52) U.S. Cl. .......................................... 514/290; 546/93
(58) Field of Search ............................ 514/290; 546/93

(56) References Cited

U.S. PATENT DOCUMENTS 4,282,233 A  8/1981 Villani ........................ 424/267
4,659,716 A  4/1987 Villani et al. ................ 514/290

OTHER PUBLICATIONS

The Merck Index, Eleventh Edition, p. 877, item No. 5455, 1989.*

* cited by examiner

Primary Examiner—Alan L. Rotman
(74) Attorney, Agent, or Firm—Thomas D. Hoffman

(57) ABSTRACT

Crystalline polymorphs of 8-chloro-6,11-dihydro-11-(4-piperidylene)-5H-benzo[5,6]cycloheptic[1,2-b]pyridine represented by the formula

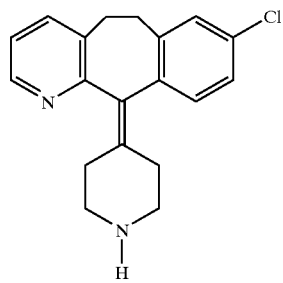

pharmaceutical compositions containing such polymorphs, and methods of using such polymorphs to treat allergic reactions in mammals such as man are disclosed.

18 Claims, 2 Drawing Sheets

8-CHLORO-6,11-DIHYDRO-11-(4-PIPERIDYLIDINE)-5H-BENZO[5,6]CYCLOHEPTA[1-2-B] PYRIDINE

This application claims the benefit of 60/051,547, field Jul. 2, 1997.

BACKGROUND OF THE INVENTION

This invention relates to crystalline polymorphs of 8-chloro-6,11-dihydro-11-(4-piperidylidene)-5H-benzo[5,6]cyclohepta[1,2-b]pyridine (hereinafter "descarbonylethoxyloratadine") represented by the formula pharmaceutical compositions containing such polymorphs, and methods of using such polymorphs to treat allergic reactions in mammals.

U.S. Pat. No. 4,659,716 discloses descarbonylethoxyloratadine which possesses antihistaminic properties with substantially no sedative properties. This U.S. Patent also discloses methods of making descarbonylethoxyloratadine and using it to treat allergic reactions in mammals.

To prepare pharmaceutical compositions containing descarbonylethoxyloratadine for administration to mammals in accordance with exacting health registration requirements of the U.S. and international health registration authorities, e.g. the FDA's Good Manufacturing Practices("GMP") requirements, there is a need to produce descarbonylethoxyloratadine in as pure a form as possible, especially a form having constant physical properties.

SUMMARY OF THE INVENTION

We have discovered that descarbonylethoxyloratadine can exist in the form of two distinct crystalline polymorphs, each having distinctly different physical properties.

Accordingly, this invention provides crystalline polymorph form 1 descarbonylethoxyloratadine essentially free of polymorph form 2 and characterized by the following x-ray powder diffraction pattern having characteristic peaks expressed in terms of "d" spacing and relative intensities ("RI") at approximately:

| d spacing (±0.04) | RI |
| --- | --- |
| 9.04 | Weak |
| 6.42 | Weak |
| 5.67 | Weak |
| 5.02 | Weak |
| 3.58 | Weak |

This invention also provides crystalline polymorph form 1 descarbonylethoxyloratadine essentially free of polymorph form 2 and characterized by the following x-ray powder diffraction pattern essentially free of poymorph form 2 and having characteristic peaks expressed in terms of "d" spacings and relative intensities ("RI")(s=strong, m=medium, w=weak, v=very and d=diffuse) at approximately:

| d spacing | RI |
| --- | --- |
| 9.04 | W |
| 7.24 | M |
| 7.11 | VWD |
| 6.69 | M |
| 6.42 | W |
| 6.02 | W |
| 5.84 | VW |
| 5.67 | W |
| 5.02 | W |
| 4.73 | M |
| 4.54 | W |
| 4.48 | W |
| 4.40 | M |
| 4.29 | WD |
| 4.25 | W |
| 4.18 | VS |
| 3.72 | W |
| 3.68 | W |
| 3.63 | W |
| 3.58 | W |
| 3.52 | M |
| 3.45 | W |
| 3.37 | S |
| 3.23 | W |
| 3.19 | M |
| 3.14 | VWD |
| 3.10 | VWD |
| 3.04 | M |
| 2.99 | VWD |
| 2.93 | VWD |
| 2.87 | VWD |
| 2.84 | W |
| 2.79 | VWD |
| 2.73 | VWD |
| 2.70 | VWD |
| 2.65 | W |
| 2.57 | VWD |
| 2.56 | VWD |
| 2.55 | VWD |
| 2.51 | VWD |
| 2.48 | VWD |
| 2.47 | VWD |
| 2.44 | VWD |
| 2.42 | WD |
| 2.37 | VWD |
| 2.34 | WD |
| 2.32 | WD |
| 2.29 | VWD |
| 2.27 | W |

This invention further provides crystalline polymorph form 2 descarbonylethoxyloratadine substantially free of poymorph form 1 and characterized by the following x-ray powder diffraction pattern having characteristic peaks expressed in terms of "d" spacing and relative intensities ("RI") approximately:

| d spacing (+ 0.04) | RI |
| --- | --- |
| 8.34 | Weak |
| 6.87 | Medium |
| 6.20 | Medium |
| 4.90 | Medium |

This invention also provides crystalline polymorph form 2 descarbonylethoxyloratadine substantially free of poymorph form 1 and characterized by the following x-ray powder diffraction having characteristic peaks expressed in terms of "d" spacing and relative intensities ("RI") s=strong, m=medium, w=weak, v=very and d=diffuse) at approximately:

| d spacing | RI |
|---|---|
| 8.34 | W |
| 7.21 | W |
| 6.87 | M |
| 6.75 | M |
| 6.20 | M |
| 6.04 | M |
| 5.91 | VW |
| 4.90 | M |
| 4.71 | M |
| 4.64 | M |
| 4.50 | WD |
| 4.39 | VS |
| 4.34 | S |
| 4.19 | VWD |
| 4.08 | W |
| 3.95 | S |
| 3.84 | M |
| 3.66 | S |
| 3.52 | W |
| 3.46 | W |
| 3.45 | WD |
| 3.39 | W |
| 3.25 | S |
| 3.18 | W |
| 3.11 | W |
| 3.07 | M |
| 2.95 | W |
| 2.88 | WD |
| 2.81 | WD |
| 2.79 | WD |
| 2.72 | VW |
| 2.59 | VW |
| 2.51 | WD |
| 2.45 | VWD |
| 2.40 | VWD |
| 2.38 | VWD |
| 2.32 | VWD |
| 2.30 | VWD |

DETAILED DESCRIPTION OF THE INVENTION

By the phrase "polymorph form 1 essentially free of polymorph form 2" as used herein means that descarbonylethoxy-loratadine polymorph form 1 prepared in accordance with this invention contains less than about 1% of form 2 as measured by infrared spectral analysis on a FTIR spectrometer. The polymorph form 1 prepared in accordance with Examples 1 and 2 had no detectable amount of form 2 by FTIR spectrophotometry. By the phrase "polymorph form 2 substantially free of polymorph form 1" as used herein means that the descarbonylethoxyloratadine polymorph form 2 prepared in accordance with this invention contains less than about 15%, preferably less than about 10%, and more preferably less than about 5–8% of form 1 as measured by infrared spectral analysis on a FTIR spectrometer.

Descarboxyloratine prepared as described in U.S. Pat. No. 4,659,716 was isolated as the acetic acid salt (Example III) and as a mixture of polymorphs of the free base from hexane (see Examples V+VI).

We have discovered that descarbonylethoxyloratadine exists as a mixture of polymorphs. Such a mixture could lead to production of a descarbonylethoxyloratadine product which would exist as a variable mixture of variable composition (i.e., variable percent amounts of polymorphs) having variable physical properties, a situation unacceptable in view of stringent GMP requirements.

We have discovered specific solvents and experimental conditions which consistently produce two distinctly different crystalline polymorphs of descarbonylethoxyloratadine thereby allowing commercial production of a consistent pharmaceutical product having constant physical properties.

In the course of developing pure descarbonylethoxyloratadine crystalline polymorphs for a pharmaceutical composition prepared in compliance with exacting GMP regulations, we tried many solvent systems, most of which produced only mixtures of polymorphs. Surprisingly we discovered that certain alcoholic solvents, e.g., hexanol and methanol produced 100% polymorph form 1, but others, e.g., 3-methyl-1-butanol and cyclohexanol produced significant amounts of form 2. Chlorinated solvents, e.g., dichloromethane produced form 1 substantially free of form 2 but the compounds were discolored. Ether solvents such as dioxane produced form 1 substantially free of form 2 but other alkane ethers,, e.g., di-isopropyl ether produced form 1 with significant amounts of form 2 and di-n-butyl ether favored formation of form 2. Ketones such as methyl isobutyl ketone produced crystalline polymorph form 1 essentially free of form 2 but methyl butyl ketone produced a 8:1 ratio of form 1 to form 2. Use of methyl isobutyl ketone is preferred to produce crystalline polymorph form 1 essentially free of form 2.

Only ethyl acetate and di-n-butyl ether were found to produce crystalline polymorph form 2 substantially free of form 1. Use of di-n-butyl ether is preferred for producing crystalline form 2 substantially free of form 1.

Figure 1:
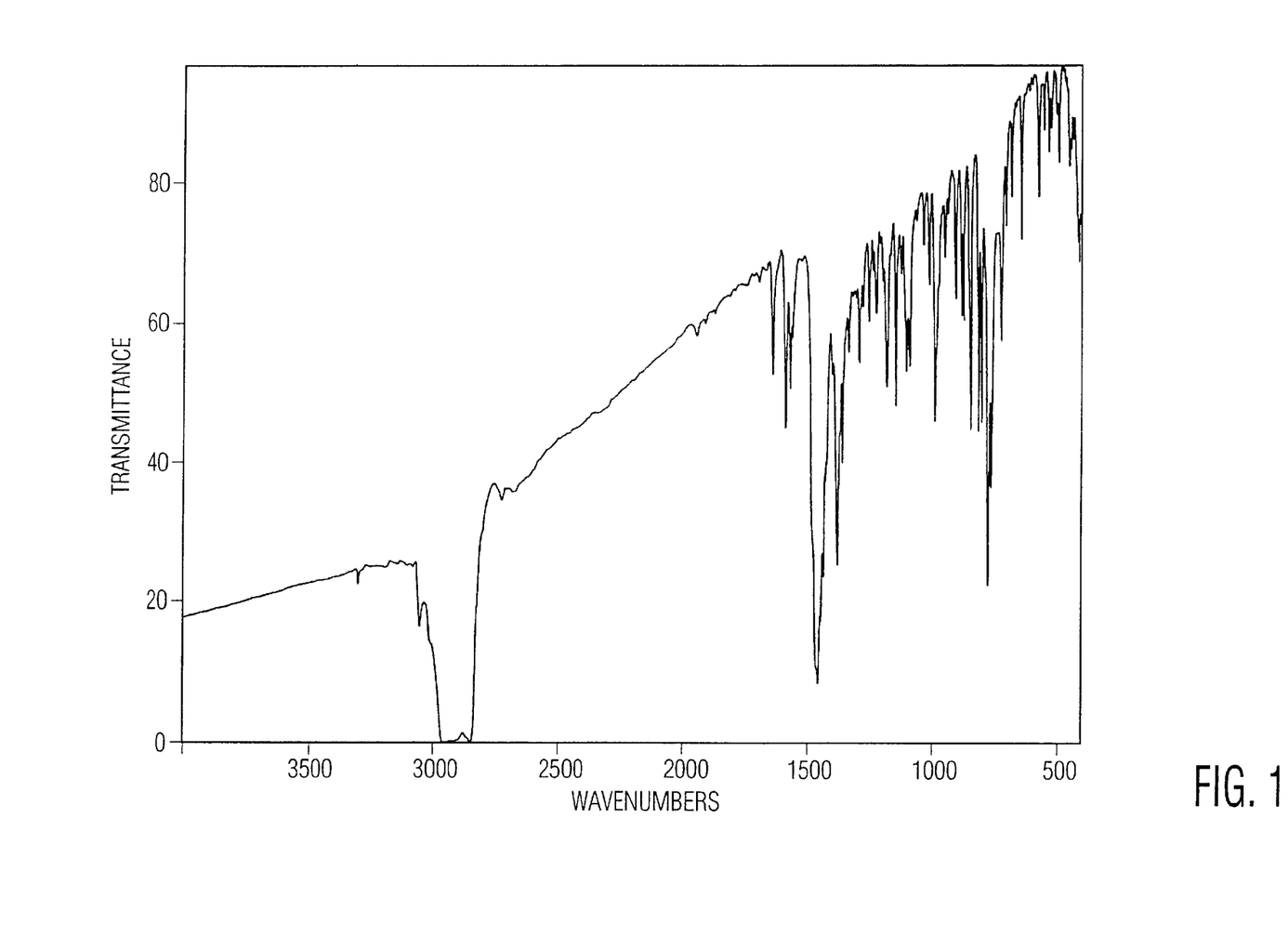
FIG. 1 presents the infrared spectrum of crystalline polymorph form 1 descarbonylethoxyloratadine as a mull in mineral oil.

The infrared spectrum of crystalline polymorph form 1 descarbonylethoxyloratadine taken on as a mull in mineral oil is characterized by the following three characteristic peaks(in reciprocal centimeters) not found in pure polymorph form 2 at approximately:

frequency ($cm^{-1}$)
3303
1290
803
780

A more complete infrared spectrum of crystalline polymorph form 1 descarbonylethoxyloratadine taken as a mull in mineral oil is characterized by the following characteristic peaks(in reciprocal centimeters) at approximately:

| frequency ($cm^{-1}$) |
|---|
| 3303 |
| 3052 |
| 3012 |
| 1636 |
| 1586 |
| 1566 |
| 1357 |
| 1331 |

-continued

| frequency (cm⁻¹) |
|---|
| 1290 |
| 1273 |
| 1249 |
| 1231 |
| 1219 |
| 1201 |
| 1190 |
| 1177 |
| 1142 |
| 1119 |
| 1100 |
| 1086 |
| 1057 |
| 1029 |
| 1008 |
| 987 |
| 946 |
| 934 |
| 906 |
| 882 |
| 873 |
| 847 |
| 816 |
| 803 |
| 780 |
| 767 |
| 726 |
| 703 |
| 681 |
| 642 |
| 572 |
| 549 |
| 530 |
| 520 |
| 498 |
| 490 |
| 449 |

Figure 2:
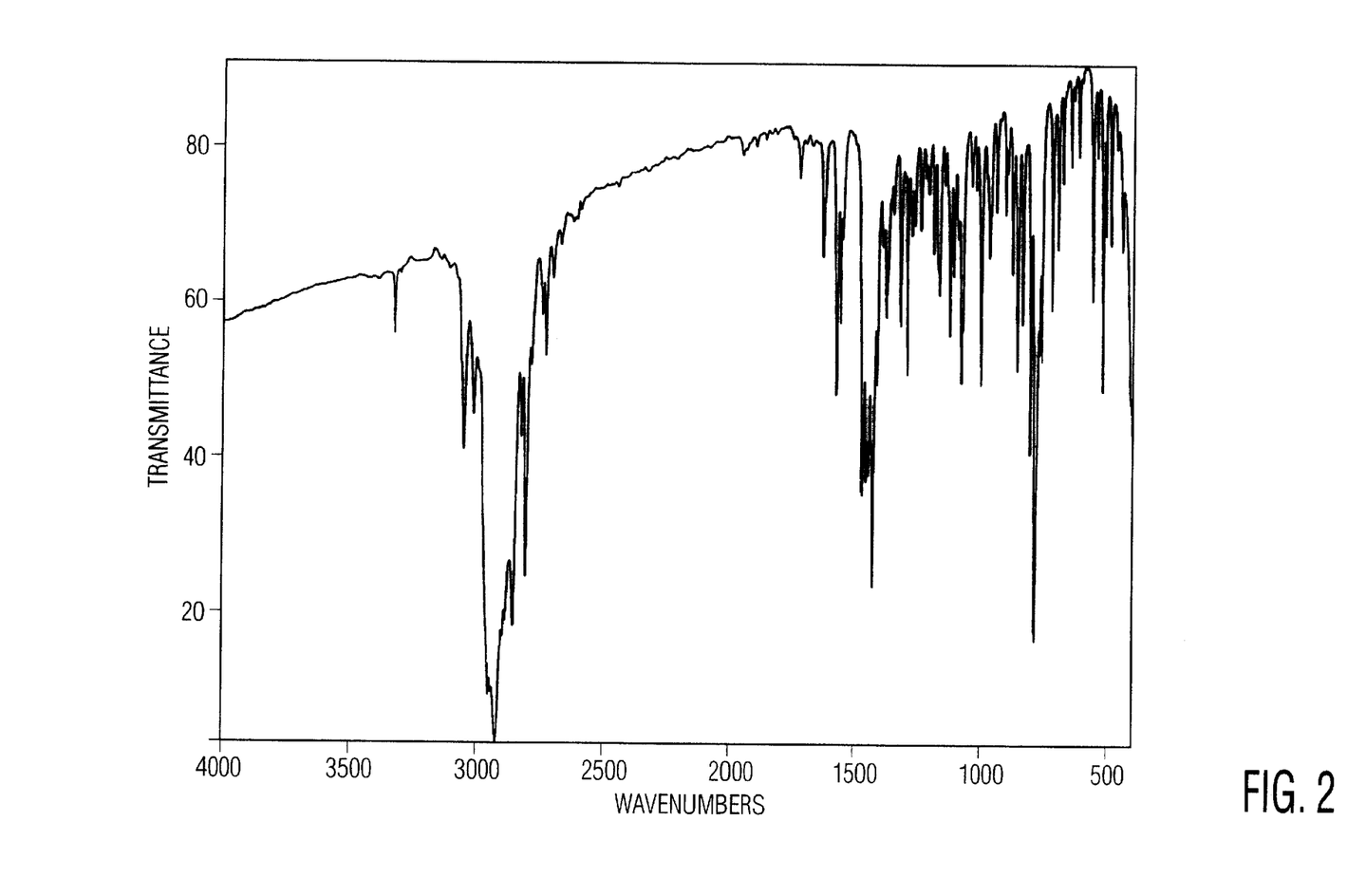
FIG. 2 presents an infrared spectrum of crystalline polymorph form 2 descarbonylethoxyloratadine as a mull in mineral oil.

The infrared spectrum of crystalline polymorph form 2 descarbonylethoxyloratadine taken as a mull in mineral oil is characterized by the following five characteristic peaks(in reciprocal centimeters) not found in the polymorph form 1 at approximately:

frequency (cm⁻¹)
3326 frequency (cm⁻¹)
1153
1133
795
771
655

A more complete infrared spectrum of crystalline polymorph form 2 descarbonylethoxyloratadine taken as a mull in mineral oil is characterized by the following characteristic peaks(in reciprocal centimeters at approximately:

| frequency (cm⁻¹) |
|---|
| 3326 |
| 3304 |
| 3052 |
| 3015 |
| 1635 |
| 1586 |
| 1569 |
| 1558 |
| 1479 |
| 1456 |
| 1437 |

-continued

| frequency (cm⁻¹) |
|---|
| 1420 |
| 1398 |
| 1383 |
| 1328 |
| 1301 |
| 1282 |
| 1265 |
| 1250 |
| 1199 |
| 1174 |
| 1153 |
| 1133 |
| 1118 |
| 1089 |
| 1010 |
| 977 |
| 951 |
| 915 |
| 887 |
| 868 |
| 846 |
| 816 |
| 795 |
| 781 |
| 771 |
| 730 |
| 707 |
| 688 |
| 655 |
| 623 |
| 570 |
| 550 |
| 528 |
| 515 |
| 493 |
| 467 |
| 447 |

These infrared spectra were obtained on mulls in mineral oil measured a Mattson Galaxy 6021 FTIR spectrometer. The mineral oil mulls were prepared and placed between NaCl or KBr plates in accordance with the USP procedure <197M>. See also "Experiments in Techniques of OInfrared Spectroscopy", R. W. Hannah and J. S. Swinehart, Perkin-Elmer Corpation, September,1974, pps, 6-1 to 6-6. The spectral data was presented in absorbance from about 3370 to 3250 cm⁻¹. The area of the peaks at 3326 ±1 cm⁻¹ (form 2) and at 3303±1 cm⁻¹ (form 1) were integrated to obtain the ratio of form 2 to form 1.

The x-ray powder diffraction patterns were measured on a Philips APD3720 automated diffractometer system (model PW 1800). The radiation source was copper (K-alpha) and the long fine focus tube connected to a Philips XRG 3100 x-ray generator operated at 45 KV and 40 mA. The take-off angle was 6 degrees and a graphite monochromator as used. A scintillation detector was employed and data was acquired with a scan rate of 0.025 degrees per second, a step size of 0.010 and a step time of 40 seconds per degree.

The x-ray powder diffraction pattern distinctive for crystalline polymorph form 1 descarbonylethoxyloratadine having characteristic peaks expressed in terms of "d" spacing and relative intensities("RI") is provided hereinbelow:

| "d" spacing (±0.04) | RI |
|---|---|
| 9.04 | Weak |
| 6.42 | Weak |

| "d" spacing (±0.04) | RI |
|---|---|
| 5.67 | Weak |
| 5.02 | Weak |
| 3.58 | Weak |

A more complete x-ray powder diffraction pattern for crystalline polymorph form 1 descarbonylethoxyloratadine having characteristic peaks expressed in terms of "d" spacing and relative intensities("RI") is provided hereinbelow:

| d spacing | RI |
|---|---|
| 9.04 | W |
| 7.24 | M |
| 7.11 | VWD |
| 6.69 | M |
| 6.42 | W |
| 6.02 | W |
| 5.84 | VW |
| 5.67 | W |
| 5.02 | W |
| 4.73 | M |
| 4.54 | W |
| 4.48 | W |
| 4.40 | M |
| 4.29 | WD |
| 4.25 | W |
| 4.18 | VS |
| 3.72 | W |
| 3.68 | W |
| 3.63 | W |
| 3.58 | W |
| 3.52 | M |
| 3.45 | W |
| 3.37 | S |
| 3.23 | W |
| 3.19 | M |
| 3.14 | VWD |
| 3.10 | VWD |
| 3.04 | M |
| 2.99 | VWD |
| 2.93 | VWD |
| 2.87 | VWD |
| 2.84 | W |
| 2.79 | VWD |
| 2.73 | VWD |
| 2.70 | VWD |
| 2.65 | W |
| 2.57 | VWD |
| 2.56 | VWD |
| 2.55 | VWD |
| 2.51 | VWD |
| 2.48 | VWD |
| 2.47 | VWD |
| 2.44 | VWD |
| 2.42 | WD |
| 2.37 | VWD |
| 2.34 | WD |
| 2.32 | WD |
| 2.29 | VWD |
| 2.27 | W |

The x-ray powder diffraction pattern distinctive for crystalline polymorph form 2 having characteristic peaks expressed in terms of "d" spacing and relative intensities ("RI") is provided hereinbelow:

| d spacings (± 0.04) | RI |
|---|---|
| 8.34 | Weak |
| 6.87 | Medium |
| 6.30 | Medium |
| 4.90 | Medium |

A more complete x-ray powder diffraction pattern for polymorph form 2 descarbonylethoxyloratadine having characteristic peaks expressed in terms of "d" spacing and relative intensities("RI") is provided hereinbelow:

| d spacing | RI |
|---|---|
| 8.34 | W |
| 7.21 | W |
| 6.87 | M |
| 6.75 | M |
| 6.20 | M |
| 6.04 | M |
| 5.91 | VW |
| 4.90 | M |
| 4.71 | M |
| 4.64 | M |
| 4.50 | WD |
| 4.39 | VS |
| 4.34 | S |
| 4.19 | VWD |
| 4.08 | W |
| 3.95 | S |
| 3.84 | M |
| 3.66 | S |
| 3.52 | W |
| 3.46 | W |
| 3.45 | WD |
| 3.39 | W |
| 3.25 | S |
| 3.18 | W |
| 3.11 | W |
| 3.07 | M |
| 2.95 | W |
| 2.88 | WD |
| 2.81 | WD |
| 2.79 | WD |
| 2.72 | VW |
| 2.59 | VW |
| 2.51 | WD |
| 2.45 | VWD |
| 2.40 | VWD |
| 2.38 | VWD |
| 2.32 | VWD |
| 2.30 | VWD |

Pharmaceutical Compositions

Pharmaceutical compositions of this invention may contain in addition to an anti-allergically effective amount of crystalline polymorph form 1 or form 2 descarbonylethoxyloratadine as the active ingredient, inert pharmaceutically acceptable carriers that may be solids or liquids. Solid form compositions include powders, tablets, dispersible granules, capsules, cachets, and suppositories. A solid carrier can be one or more substances which may also act as diluants, flavoring agents, solubilizers, lubricants, suspending agents, binders or tablet disintegration agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from about 5 to about 20 percent of the active ingredient. Suitable solid carriers are magnesium carbonate, magnesium stearate, talc, sugar, lactose, pectin, dextrin, starch, gelatin, tragacanth, methycelulose, sodium carboxymethylcellulose, a low melting wax. cocoa butter and the like. The term "compositions" is intended to include the formulation of the active compound with encapsulating material as carrier providing a capsule in which the active component (with or without other carriers) is surrounded by carrier, which is thus in association with it. Similarly, caches are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for topical administration. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can e made by dispersing the finely divided active component in water with viscous material, i.e., natural or synthetic gums, resins, methylcellulose, sodium carboxymethylcellulose and other well-known suspending agents.

Topical formulation useful for nasal or ophthalmic administration are also contemplated. Topical formulation suitable for nasal administration may be solutions or suspensions. Ophthalmic formulations may be solutions, suspension or ointments. Ointments usually contain lipophilic carriers such as mineral oil and/or petrolatum. Solution for ophthalmic administration may contain sodium chloride, acid and/or base to adjust the pH as well as purified water and preservatives.

The anti-allergic effective amount of polymorph form 1 or form 2 descarbonylethoxyloratadine for topical administration varies from 0.1 to 5% by weight of the total pharmaceutical composition. The preferred amount varies from 0.5 to 2% by weight of the total pharmaceutical composition.

The anti-allergic effective amount of polymorph form 1 or form 2 descarbonylethoxyloratadine for oral administration varies from about 1 to 50 mg/day, preferably about 2.5 to 20 mg/day and more preferably about 5 to 10 mg/day in single or divided doses. The most preferred amount is 5.0 mg, once a day.

Of course the precise dosage and dosage regimen may be varied depending upon the requirements of the patients. (e.g.. his or her sex, age) as well as the severity of the allergic condition being treated. Determination of the proper dosage and dosage regimen for a particular patient will be within the skill of the attending clinician.

The polymorph form 1 and form 2 descarbonylethoxyloratadine possess antihistaminic properties. These antihistaminic properties have been demonstrated in standard animal models, such as prevention of histamine—induced lethality in guinea pigs. Antihistaminic activity of form 1 and form 2 has also been demonstrated in a monkey model.

EXAMPLE 1

Preparation of Polymorph Form 1 Descarbonylethoxyloratadine

To a solution of 60.0 kg of potassium hydroxide flakes in 200 liters of industrial methylated spirits was added 50.0 kg of loratadine (available from Schering Corporation, Kenilworth, N.J., see also U.S. Pat. No. 4,282,233). The so-formed mixture was heated under reflux for 3 hours and 150 liters of water were added. The so-formed mixture was distilled at atmospheric pressure until a temperature of the mixture reached 108° C. The mixture was cooled to 68° C. and 150 liters of methyl isobutyl ketone (MIBK) were added and the mixture was agitated until all the solids were dissolved. The organic layer was separated and washed with water at 80° C. until the separated aqueous layer had a pH of 9. Fifty (50) liters of MIBK were then removed from the organic layer by distillation at atmospheric pressure and the so formed organic layer was cooled to around 0° C. for 1 hour. The resulting crystalline product was separated by centrifugation, washed with 2×12 liters of room temperature MIBK and spun dry in a centrifuge at high speed. The so-formed product was dried at 60° C. for 6 hours to give 29.05 kg of polymorph form 1 descarbonylethoxyloratadine as a white crystalline solid, mp 156.8–157.7. The structure of the title compound was confirmed by comparison of its IR and NMR with spectra of a reference standard.

EXAMPLE 2

Preparation of Polymorph Form 1 Descarbonylethoxyloratadine

Loratadine (45 Kg, 117 moles) was refluxed in about 180 liters of ethanol containing potassium hydroxide (about 40.5 Kg, excess) for about 5 hours to complete the carbomate hydrolysis (see also Example VI of U.S. Pat. No. 4,659,716). The warm reaction mixture was diluted with about 135 liters of water and distilled at atmospheric pressure until a reaction mixture temperature of 105–110° C. was achieved. The reaction mixture was than cooled to 50–70° C., diluted with about 135 liters of methyl isobutyl ketone (MIBK), and the so-formed mixture was reheated to 80–90° C. to redissolve solids. The aqueous layer was separated, and the MIBK layer was washed with additional portions of water until a pH of 6–9 was achieved in the aqueous layer.

The MIBK layer was then concentrated under atmospheric pressure and slowly cooled to −5 to 0° C. as crude descarbonylethoxyloratadine crystallized. Crude descarbonylethoxyloratadine was filtered, washed with MIBK, and dried at about 60° C. to produce about 33.5 Kg (92% of theory) of crude descarbonyl-ethoxyloratadine which may also be carried into the next step as a wet cake.

Crude descarbonylethoxyloratadine (33.6 Kg, 108 moles) was dissolved in about 135 liters of hot (85–95° C.) MIBK, filtered, and about 50 liters of the MIBK was distilled from the mixture at atmospheric pressure. The so-formed solution was then slowly cooled to 15–22° C., aged for about an hour, and the resulting crystalline slurry of descarbonylethoxyloratadine was filtered, washed with MIBK, and dried at about 80° C. to produce 31 Kg (92% yield) of polymorph form 1 descarbonylethoxyloratadine as a white crystalline solid. This white crystalline solid contained 100% of form I, with no detectable amount of form 2 by FTIR spectrophotometry.

Crystalline polymorph form 1 was micronized using a fluid energy mill and packaged in double polyethylene bags in a fiber drum closed with a metal ring.

EXAMPLE 3

Alternative Preparations of Polymorph Form 1 Descarbonylethoxyloratadine

A. To a 50 mL Erlenmeyer flask was added 3.3 g of descarbonylethoxyloratadine (prepared in accordance with Example VI of U.S. Pat. No. 4,659,716) and methanol (3.5 ml). The so-formed mixture was heated until complete dissolution was obtained. The so-formed clear solution was allowed to cool slowly to room temperature and kept at room temperature for 4 hours. The resulting crystalline product was filtered, washed with hexane (10 ml) and dried in a vacuum oven at 40° C. under nitrogen for 24 hours to provide 2.77 g of polymorph form 1 descarbonylethoxyloratadine as a white crystalline solid, (DSC 157.30).

B. To a 250 mL three neck round bottom flask equipped with an overhead agitator, thermocouple and nitrogen gas source was added 10 g of descarbonylethoxyloratadine (prepared as described in Example VI of U.S. Pat. No. 4,65,716) and 60 mL of MIBK. The so-formed mixture was heated to 105° C. and the temperature was maintained at 105° C. until complete dissolution was obtained. The so-formed solution was slowly cooled to room temperature to allow the crystalline product to precipitate out of solution. The so-formed mixture was cooled to 5° C. and the temperature was maintained at 5° C. for 1 hour. The solid was vacuum filtered and washed with 2 volumes of MIBK (chilled to 5° C.). The solid was dried in an oven at 50° C. until the loss on drying was 0.4% or less. 8.30 g of polymorph form 1 descarbonylethoxyloratadine (100% by FTIR spectrophotometry) was obtained as a white crystalline solid.

EXAMPLE 4

Preparation of Polymorph Form 2 Descarbonylethoxyloratadine

A solution of 366 g of descarbonylethoxyloratadine (prepared as described in Example VI of U.S. Pat. No. 4,65,716) in 3 liters of ethyl acetate was heated to reflux; 15 g of Darco decolorizing charcoal and 25 g of Supercel filtering aid were added and the so-formed mixture was further refluxed for 10 minutes. The mixture was filtered while hot through a Supercel filter mat. The filtrate was concentrated at elevated temperature to 650 ml. The so-formed concentrated filtrate was rapidly cooled to 0° C. The resulting precipitate was filtered, washed with hexane and dried in an air-draft oven at 55–60° C. to give 333.2 g of polymorph form 2 descarbonylethoxyloratadine as a white crystalline solid, having mp 154.0–155.5° C., and containing 100% form 2 by FTIR spectrophotometry.

EXAMPLE 5

Alternative Preparation of Polymorph Form 2 Descarbonylethoxyloratadine

To a first 250 mL three neck round bottom flask ("first flask")equipped with an overhead agitator, thermocouple and nitrogen gas source was added 10g of descarbonylethoxyloratadine (prepared as described in Example VI of U.S. Pat. No. 4,65,716) and 150 mL of di-n-butyl ether. The so-formed mixture was heated to 100° C. and held at this temperature until all solid material dissolved, and a clear solution was formed. To a second 250 mL three neck round bottom flask("second flask") equipped identically as the first flask was added 50 mL of di-n-butyl ether. The second flask was cooled to −50° C. A cendula was connected to both flasks and the ends of the cendula were placed below the surface of the solutions in both flasks. Nitrogen pressure was applied to the first flask sufficient to completely force the solution in first flask into the second flask. The temperature of the second flask was maintained at below −20° C. and the so-formed very turbid solution in the second flask was stirred for five minutes. The resulting precipitate was vaccum filtered. The solid was dried in a vaccum oven under a nitrogen atmosphere at room temperature. No heat was applied to prevent discoloration of the product. Seven grams (7 g) of polymorph form 2 descarbonylethoxyloratadine was obtained as a crystalline solid which contained 92% (±5%) of form 2 by FTIR spectrophotometry.

Stability Testing for Crystalline Polymorph Form 1

Samples of crystalline polymorph form 1 prepared in accordance with this invention were subjected to stability testing at various temperatures (25, 30 and 40° C.) and relative humidities of 60%, 60% and 75%, respectively. Assay for form 1 and total related compounds were performed including. physical appearance, X-ray diffraction, FTIR (identity), FTIR (polymorph ratio) and pH. No significant change (<1%) from initial sample % form 1 and related compounds was observed.

What is claimed is:

1. Crystalline polymorph form 1 descarbonylethoxyloratadine essentially free of polymorph form 2 and characterized by the following x-ray powder diffraction pattern having characteristic peaks expressed in terms of "d" spacing and relative intensities("RI") at approximately:

| d spacing (±0.04) | RI |
|---|---|
| 9.04 | Weak |
| 6.42 | Weak |
| 5.67 | Weak |
| 5.02 | Weak |
| 3.58 | Weak. |

2. Crystalline polymorph form 1 descarbonylethoxyloratadine essentially free of polymorph form 2 and characterized by the following x-ray powder diffraction pattern having characteristic peaks expressed in terms of "d" spacing and relative intensities("RI") (s=strong, m=medium, w=weak, v=very and d=diffuse) at approximately:

| d spacing | RI |
|---|---|
| 9.04 | W |
| 7.24 | M |
| 7.11 | VWD |
| 6.69 | M |
| 6.42 | W |
| 6.02 | W |
| 5.84 | VW |
| 5.67 | W |
| 5.02 | W |
| 4.73 | M |
| 4.54 | W |
| 4.48 | W |
| 4.40 | M |
| 4.29 | WD |
| 4.25 | W |
| 4.18 | VS |
| 3.72 | W |
| 3.68 | W |
| 3.63 | W |
| 3.58 | W |
| 3.52 | M |
| 3.45 | W |
| 3.37 | S |
| 3.23 | W |
| 3.19 | M |

| d spacing | RI |
|---|---|
| 3.14 | VWD |
| 3.10 | VWD |
| 3.04 | M |
| 2.99 | VWD |
| 2.93 | VWD |
| 2.87 | VWD |
| 2.84 | W |
| 2.79 | VWD |
| 2.73 | VWD |
| 2.70 | VWD |
| 2.65 | W |
| 2.57 | VWD |
| 2.56 | VWD |
| 2.55 | VWD |
| 2.51 | VWD |
| 2.48 | VWD |
| 2.47 | VWD |
| 2.44 | VWD |
| 2.42 | WD |
| 2.37 | VWD |
| 2.34 | WD |
| 2.32 | WD |
| 2.29 | VWD |
| 2.27 | W. |

3. The crystalline polymorph form 1 descarbonylethoxy-loratadine of claim 1 further characterized by an infrared spectrum generated on a mull of the polymorph form 1 in mineral oil showing the following characteristic peaks in reciprocal centimeters at approximately:

frequency (cm$^{-1}$)
3303
1290
803
780.

4. The crystalline polymorph form 1 descarbonylethoxy-loratadine of claim 1 further characterized by an infrared spectrum generated on a mull of the polymorph form 1 in mineral oil showing the following characteristic peaks in reciprocal centimeters at approximately:

| frequency (cm$^{-1}$) |
|---|
| 3303 |
| 3052 |
| 3012 |
| 1636 |
| 1586 |
| 1566 |
| 1357 |
| 1331 |
| 1290 |
| 1273 |
| 1249 |
| 1231 |
| 1219 |
| 1201 |
| 1190 |
| 1177 |
| 1142 |
| 1119 |
| 1100 |
| 1086 |
| 1057 |
| 1029 |
| 1008 |
| 987 |
| 946 |
| 934 |
| 906 |
| 882 |
| 873 |
| 847 |
| 816 |
| 803 |
| 780 |
| 767 |
| 726 |
| 703 |
| 681 |
| 642 |
| 572 |
| 549 |
| 530 |
| 520 |
| 498 |
| 490 |
| 449. |

5. The crystalline polymorph form 1 descarboxy loratadine of characterized by an infrared spectrum generated on a mull of said polymorph form 1 in mineral oil showing the following characteristic peaks in reciprocal centimeters at approximately:

frequency (cm$^{-1}$)
3303
1290
803
780.

6. The crystalline polymorph form 1 decarbonylethoxy-loratadine of claim 2 which is further characterized by infrared spectrim generated on a mull of said polymorph form 1 in mineral oil showing the following characteristic peaks in reciprocal approximately:

| frequency (cm$^{-1}$) |
|---|
| 3303 |
| 3052 |
| 3012 |
| 1636 |
| 1586 |
| 1566 |
| 1357 |
| 1331 |
| 1290 |
| 1273 |
| 1249 |
| 1231 |
| 1219 |
| 1201 |
| 1190 |
| 1177 |
| 1142 |
| 1119 |
| 1100 |
| 1086 |
| 1057 |
| 1029 |
| 1008 |
| 987 |
| 946 |
| 934 |
| 906 |
| 882 |
| 873 |
| 847 |
| 816 |

-continued

| frequency (cm$^{-1}$) |
| --- |
| 803 |
| 780 |
| 767 |
| 726 |
| 703 |
| 681 |
| 642 |
| 572 |
| 549 |
| 530 |
| 520 |
| 498 |
| 490 |
| 449. |

7. A pharmaceutical composition comprising an antiallergic effective amount of the crystalline polymorph form 1 descarbonylethoxyloratadine of claim 1 and a pharmaceutically acceptable carrier.

8. Crystalline polymorph form 2 descarbonylethoxyloratadine substantially free of polymorph form 1 and characterized by the following x-ray powder diffraction pattern having characteristic peaks expressed in terms of "d" spacing and relative intensities("RI") at approximately:

| d spacing (± 0.04) | RI |
| --- | --- |
| 8.34 | Weak |
| 6.87 | Medium |
| 6.20 | Medium |
| 4.90 | Medium. |

9. Crystalline polymorph form 2 descarbonylethoxyloratadine substantially free of polymorph form 1 and characterized by the following x-ray powder diffraction pattern having characteristic peaks expressed in terms of "d" spacings and relative intensities ("RI")(s=strong, m=medium, w=weak, v=very and d=diffuse) at approximately:

| d spacing | RI |
| --- | --- |
| 8.34 | W |
| 7.21 | W |
| 6.87 | M |
| 6.75 | M |
| 6.20 | M |
| 6.04 | M |
| 5.91 | VW |
| 4.90 | M |
| 4.71 | M |
| 4.64 | M |
| 4.50 | WD |
| 4.39 | VS |
| 4.34 | S |
| 4.19 | VWD |
| 4.08 | W |
| 3.95 | S |
| 3.84 | M |
| 3.66 | S |
| 3.52 | W |
| 3.46 | W |
| 3.45 | WD |
| 3.39 | W |
| 3.25 | S |
| 3.18 | W |
| 3.11 | W |
| 3.07 | M |
| 2.95 | W |
| 2.88 | WD |
| 2.81 | WD |
| 2.79 | WD |
| 2.72 | VW |
| 2.59 | VW |
| 2.51 | WD |
| 2.45 | VWD |
| 2.40 | VWD |
| 2.38 | VWD |
| 2.32 | VWD |
| 2.30 | VWD. |

10. The crystalline polymorph form 2 descarboxy loratadine of claim 8 further characterized by an infrared spectrum generated on a mull of said polymorph form 2 in mineral oil showing the following characteristic peaks in reciprocal centimeters at approximately:

frequency (cm$^{-1}$)
3326
1153
795
771
655.

11. The crystalline polymorph form 2 descarbonylethoxyloratadine of claim 8 further characterized by an infrared spectrum generated on a mull of said polymorph form 1 in mineral oil showing the following characteristic peaks in reciprocal centimeters at approximately:

| frequency (cm$^{-1}$) |
| --- |
| 3326 |
| 3304 |
| 3052 |
| 3015 |
| 1635 |
| 1586 |
| 1569 |
| 1558 |
| 1479 |
| 1456 |
| 1437 |
| 1420 |
| 1398 |
| 1383 |
| 1328 |
| 1301 |
| 1282 |
| 1265 |
| 1250 |
| 1199 |
| 1174 |
| 1153 |
| 1133 |
| 1118 |
| 1089 |
| 1010 |
| 977 |
| 951 |
| 915 |
| 887 |
| 868 |
| 846 |
| 816 |
| 795 |
| 781 |
| 771 |

| frequency (cm⁻¹) |
| --- |
| 730 |
| 707 |
| 688 |
| 655 |
| 623 |
| 570 |
| 550 |
| 528 |
| 515 |
| 493 |
| 467 |
| 447. |

12. The crystalline polymorph form 2 descarbonylethoxy-loratadine of claim 9 further characterized by an infrared spectrum generated on a mull of said polymorph form 2 in mineral oil showing the following characteristic peaks in reciprocal centimeters at approximately:

frequency (cm⁻¹)
3326
1153
1133
795
771
655.

13. The crystallinepolymorph form 2 descarboxy loratadine of claim 9 further characterized by an infrared spectrum generated on a mull of said polymorph form 2 in mineral oil showing the following characteristic peaks in reciprocal centimeters at approximately:

| frequency (cm⁻¹) |
| --- |
| 3326 |
| 3304 |
| 3052 |
| 3015 |
| 1635 |
| 1586 |
| 1569 |
| 1558 |
| 1479 |
| 1456 |
| 1437 |
| 1420 |
| 1398 |
| 1383 |
| 1328 |
| 1301 |
| 1282 |
| 1265 |
| 1250 |

| frequency (cm⁻¹) |
| --- |
| 1199 |
| 1174 |
| 1133 |
| 1118 |
| 1089 |
| 1010 |
| 977 |
| 951 |
| 915 |
| 887 |
| 868 |
| 846 |
| 816 |
| 795 |
| 781 |
| 771 |
| 730 |
| 707 |
| 688 |
| 655 |
| 623 |
| 570 |
| 550 |
| 528 |
| 515 |
| 493 |
| 467 |
| 447. |

14. A pharmaceutical composition comprising an antiallergic amount of the crystalline polymorph form 2 descarbonylethoxyloratadine of claim 8 and a pharmaceutically acceptable carrier.

15. A pharmaceutical composition comprising an antiallergic amount of the crystalline polymorph form 2 descarbonylethoxyloratadine of claim 9 pharmaceutically acceptable carrier.

16. A pharmaceutical composition comprising an antiallergic amount of the crystalline polymorph form 1 descarbonylethoxyloratadine of claim 2 and a pharmaceutically acceptable carrier.

17. A method of treating allergic reactions in a mammal which comprises administering to said mammal an antiallergic effective amount of the crystalline polymorph form 1 descarbonylethoxyloratadine of claim 1.

18. A method of treating allergic reactions in a mammal which comprises administering to said mammal an antiallergic effective amount of the crystalline polymorph form 2 descarbonylethoxyloratadine of claim 8.

* * * * *